(12) United States Patent
Ishihara et al.

(10) Patent No.: US 6,297,280 B1
(45) Date of Patent: Oct. 2, 2001

(54) COMPOSITION AND METHOD FOR SUPPRESSING BEHAVIOR PROBLEMS OF PETS

(75) Inventors: Noriyuki Ishihara; Senji Sakanaka; Seiji Shu; Lekh Raj Juneja, all of Yokkaichi (JP)

(73) Assignee: Taiyo Kagaku Co., Ltd., Mie-ken (JP)

( * ) Notice: Subject to any disclaimer, the term of this patent is extended or adjusted under 35 U.S.C. 154(b) by 0 days.

(21) Appl. No.: 09/619,713

(22) Filed: Jul. 19, 2000

(30) Foreign Application Priority Data

Jul. 19, 1999 (JP) .................................. 11-204307

(51) Int. Cl.[7] ........................ A61K 31/195; A61K 31/20; A61K 31/14
(52) U.S. Cl. ......................... 514/563; 514/560; 514/642
(58) Field of Search ................... 514/563, 560, 514/642

(56) References Cited

PUBLICATIONS

Anan et al, Chemical Abstracts, vol. 115, No. 254726, 1991.*

Tsushida et al, Biological Abstracts, vol. 85, No. 3721, 1987.*

\* cited by examiner

*Primary Examiner*—William R Jarvis
(74) *Attorney, Agent, or Firm*—Birch, Stewart, Kolasch & Birch, LLP

(57) ABSTRACT

A composition for suppressing behavior problems of pets, comprising theanine, and optionally one or more compounds selected from the group consisting of highly unsaturated fatty acids and cholines; and a method of suppressing behavior problems of pets, comprising administering the above composition to a pet having behavior problems. The composition can be effectively used for suppressing various behavior problems associated with the pet.

6 Claims, No Drawings

COMPOSITION AND METHOD FOR SUPPRESSING BEHAVIOR PROBLEMS OF PETS

BACKGROUND OF THE INVENTION

1. Field of the Invention

The present invention relates to a composition for suppressing behavior problems of pets, and a method for suppressing behavior problems of pets using the same.

2. Discussion of the Related Art

With the popularity of owning a pet and the change of the housing situations of recent years, the method of keeping a pet has been changed. For example, regarding a dog, while it was kept as a watch dog or a hunting dog in the past, it has now been kept indoors as an indoor dog. Similarly, regarding a cat, while it was kept mainly out of the house in the past, it has now been kept mainly indoors. Also, how an owner values a pet has changed: Thinking of a pet as a companion animal that the pet is regarded as a member of family has been infiltrated in the people's mind.

Because of such changes, there arises a new disease, namely behavior problems associated with failure in pet breeding and training for keeping it indoors and also with old age.

For example, regarding the indoor dogs, there have been known to show behaviors such as attack, destruction, inappropriate elimination, licking their paws repeatedly, and excess barking. Also, regarding the cats, there have been known to show behaviors such as inappropriate elimination and scratching.

As a means to suppress these behavior problems, Japanese Patent Laid-Open No. Hei 2-308737 discloses a technique relating to an automatic training device for pets to regulate the behavior automatically such that an animal such as a pet does not go out of a certain area. However, the device has a complicated structure with a defect of complicated operation, and is undesirable from the viewpoint of protecting an animal from harm since a high voltage is applied to a pet which shows abnormal behaviors.

Also, pet owners have been instructed to ignore a dog from about 30 minutes before going out, namely to give no attention for the dog at all, and further to ignore behaviors of the dog such as gladly licking and jumping when the pet owners return home until the dog calms down. However, such a therapeutic method could be easily understood to mean that the pet owner should not have any contact with the dog at all, and when such understanding is made, the symptoms of behavior problems are likely to get rather worse.

Further, there are proposed administration of an anti-anxiety agent, a hormone agent, a tranquilizer, a sedative, an anti-epileptic agent and a pheromone as the pharmacotherapy. However, since there are problems of side effects and stresses of the pet arising from the administration of the pharmaceuticals, these proposals have not yet came into practical use.

Declaw, cutting off the claw of cat, has a problem from the viewpoint of protecting an animal from harm, and therefore is not practiced in most case.

An object of the present invention is to provide a composition for suppressing behavior problems of pets which cannot be effectively solved by the conventional methods, and a method for suppressing behavior problems using it.

The above and other objects of the present invention will be apparent from the following description.

SUMMARY OF THE INVENTION

As a result of intense research in view of suppressing the behavior problems of pets, the present inventors have found that a composition comprising a theanine, and optionally further comprising one or more compounds selected from the group consisting of highly unsaturated fatty acids and cholines can suppress the behavior problems of pets, thereby accomplishing the present invention.

Specifically, the present invention is directed to:

[1] a composition for suppressing behavior problems of pets, comprising theanine;

[2] a method of suppressing behavior problems of pets, comprising administering the composition of item [1] above to a pet having behavior problems; and

[3] use of the composition of item [1] above for suppressing behavior problems of pets.

DETAILED DESCRIPTION OF THE INVENTION

The composition for suppressing behavior problems of pets of the present invention can be used for the purpose of suppressing behavior problems of pets arising from various causes. The desired effects of the composition of the present invention is manifested on the basis of the action of suppressing behavior problems of pets found for the first time for theanine contained in the above composition.

The theanine used in the present invention is a kind of an amino acid, and is a water-soluble white crystalline powder.

Methods for preparing theanine used in the present invention may be any of known methods. Examples thereof include a method of extracting it from tea-leaves; a method of preparing it by an organic synthesis reaction [*Chem. Pharm. Bull.*, 19(7), 1301–1307 (1971)]; a method of preparing it by treating a mixture of glutamine and ethylamine with glutaminase (Japanese Examined Patent Publication No. Hei 7-55154); a method comprising culturing culture cells of tea in a medium containing ethylamine, and promoting proliferation of the culture cells, with increasing an dosage of accumulated theanine in the culture cells (Japanese Patent Laid-Open No. Hei 5-123166); and a modification method of one disclosed in Japanese Examined Patent Publication No. Hei 7-55154 and Japanese Patent Laid-Open No. Hei 5-123166 using an ethylamine derivative, such as ethylamine hydrochloride, in place of ethylamine. The term "tea-leaves" as used herein refers to green tea, oolong tea, black tea, and the like. The theanine obtained by the methods described above may be of any of L-form, D-form and DL-form, among which the L-form is preferred in the present invention, because it is approved as a food additive, and it is economically utilizable. In addition, the theanine used in the present invention may be of any forms, such as purified products, crudely purified products, extracts and commercialized products [trade names: "SUNTHEANINE" and "TEAPECUS" commercially available from Taiyo Kagaku Co., Ltd.].

From the viewpoint of enhancing an action of suppressing behavior problems of pets owned by theanine, it is preferable that the composition of the present invention further comprises one or more compounds selected from highly unsaturated fatty acids and cholines. Although the function mechanism is not clarified, the compound can act to enhance the action of suppressing behavior problems owned by theanine. Therefore, the same level of effects as that exhibited with theanine alone can be obtained, with a smaller dosage of theanine required as compared to the case where theanine is used alone by the copresence of the compound.

The term "highly unsaturated fatty acid" in the present invention refers to unsaturated fatty acids having 18 or more carbon atoms such as linoleic acid, γ-linolenic acid, dihomo-γ-linolenic acid, arachidonic acid, α-linolenic acid, eicosapentaenoic acid (EPA) and docosahexaenoic acid (DHA), among which arachidonic acid and DHA are preferable, from the viewpoint of effectively enhancing an action of suppressing behavior problems of pets owned by theanine, and DHA is more preferable.

The supplying form of the highly unsaturated fatty acid used in the composition of the present invention includes, but not particularly limited to, fats and oils containing the fatty acid and purified products of the fatty acid. In addition, for the purpose of stabilizing the fatty acid, the highly unsaturated fatty acid can be used in a combination of a functional protein preparation disclosed in Japanese Patent Laid-Open No. Hei 9-9878, to give powdery fats and oils.

Concrete examples of the forms of the highly unsaturated fatty acid are disclosed, for instance, as follows. When the highly unsaturated fatty acid is DHA, it can be in the form of DHA powdery oils and fats ["Kinoseiyushi no Funmatsu Anteika" (Stabilization by Making Powdery Form of Functional Fats and Oils), "Dai 53 Kai Nihon Eiyo Shokuryo Gakkai Koen Yoshishu" (Summary of 53rd Academic Meeting for Japanese Society of Nutrition and Food Science), p. 134 3C-02a, 1999], prepared by making the DHA powdery form with egg yolk protein. When the highly unsaturated fatty acid is arachidonic acid, it can be in the form of egg yolk oil [*Japan Food Science* 38 (1), p.31–39 (1999)].

Choline used for the composition of the present invention refers to trimethyl-β-hydroxyethyl ammonium, and it can be in the form of organic cholines, choline salts and free cholines. As the organic cholines, there can be exemplified phosphatidylcholine. As the choline salts, there can be exemplified choline chloride. In the case of phosphatidylcholine, it can be phospholipids derived from eggs or soybeans. Among them, from the same viewpoints as the case of the highly unsaturated fatty acid, phosphatidylcholine is preferable.

The pet in the present invention refers to an animal which humans keep for the fondling purpose, and concretely includes dogs, cats, rabbits, hamsters, guinea pigs, rats, mice, parakeets, parrots, Lonchura striatas and the like. The dogs and cats are preferable for the use of the composition of the present invention, from the viewpoint of the frequency of the behavior problems, and the dogs are most preferable. In addition, as the dogs, indoor dogs and aged dogs are preferable, from the viewpoint of effectively suppressing behavior problems indoors and the like.

Although a detailed cause-and-effect relationship is not yet clarified, the behavior problems in the present invention include behaviors caused by or associated with, for instance, separation anxiety, sociopathy, neurological disorders producing abnormal behavior, abnormal urine marking, heatstroke, dysautonomia, kinesia and dementia. Concrete examples thereof include conditions and behaviors such as attack, destruction, inappropriate elimination, licking its paw repeatedly, excess barking, scratching, cryptogenic astasia, shivering, astasia, spray, reduced blood pressure, abnormal appestat associated with adynamia (overeating and the like), aberrant motor behavior (excess sleeping, reversal of night and day, and the like), dysbasia (trudging, walking in a given direction and the like), abnormal elimination behavior Incontinence, housesoiling and the like), abnormal sense (decline of auditory sense, decline of olfactory sense, and the like), abnormal posture (hanging down of head and tail, abnormal posture and the like), abnormal vocalizing (monotonous and loud voice, barking in the midnight or against the abnormal subject and the like), loss of feeling (decline of body language, loss of body language and the like), loss of interrelation (loss of interrelation with other humans or other animals, loss of interrelation with the pet owner and the like) and abnormal situation judgment and the like. The composition of the present invention can be especially suitably used for suppression of behavior problems such as attack, destruction, inappropriate elimination, excess barking, aberrant motor behavior, dysbasia, reduced blood pressure, shivering, cryptogenic astasia, abnormal vocalizing, astasia, and spray.

The process for preparing the composition of the present invention is not particularly limited, as long as the composition can comprise theanine, and preferably theanine and one or more compounds selected from the group consisting of highly unsaturated fatty acids and cholines. Other ingredients constituting the composition of the present invention are not particularly limited as long as they do not impair the action of suppressing behavior problems owned by theanine.

The content of theanine in the composition of the present invention is not particularly limited. The content of theanine is preferably 0.00025 to 100% by weight. In the case where the composition of the present invention comprises both theanine and the above compound, it is preferable that the content of theanine is 0.05 to 20% by weight, and that a total content of the compounds is 50 to 99% by weight.

The method for administration of the composition of the present invention is not particularly limited, and is preferably oral administration or administration by injection, especially preferably oral administration. In case of the oral administration, a concrete method thereof includes a method comprising adding the composition to a pet food; a method comprising dissolving the composition in an electrolytic solution; a method comprising adding the composition to drinking water, and the like. Also, the composition may be administered together with a conventionally used pharmaceutical.

The timing of administration of the composition of the present invention is not particularly limited. When the composition is administered to a pet before the pet remarkably exhibits behavior problems, the prophylactic effect can be expected. On the other hand, when the composition is administered to a pet while the pet exhibits behavior problems, the behavior problems can be suppressed effectively. In addition, the period of administration of the composition of the present invention is not particularly limited.

As for the dosage of the composition in the present invention, it is not required to particularly consider age, sexual differences, and the like of pets. Here, the dosage of the composition shown below is "per administration." In an embodiment where theanine is used alone for the composition, the composition is used such that the dosage of theanine is preferably 0.05 to 100 mg, more preferably 0.07 to 80 mg, especially preferably 0.09 to 60 mg, per one kilogram of the body weight of the pet. It is preferable that the dosage of theanine is 0.05 mg or more, per one kilogram of the body weight of the pet, from the viewpoint of obtaining excellent suppressive effect on the behavior problems, and that the dosage is 100 mg or less, per one kilogram of the body weight of the pet, from the viewpoint of costs.

In addition, in an embodiment where the composition comprises theanine and one or more compounds selected from the group consisting of highly unsaturated fatty acids and cholines, the composition is used such that the dosage of theanine is preferably 0.02 to 20 mg, more preferably 0.05 to 10 mg, especially preferably 0.07 to 5 mg, per one kilogram of the body weight of the pet, and that the total dosage of compounds other than theanine is preferably 0.2 to 80 mg, more preferably 0.5 to 65 mg, especially preferably 1 to 50 mg, per one kilogram of the body weight of the pet. Thus, the composition is used such that the total dosage of whole ingredients contained in the composition is preferably 0.22 to 80 mg, more preferably 0.55 to 75 mg, especially preferably 1.07 to 55 mg, per one kilogram of the body weight of the pet. It is preferable that the total dosage of the whole ingredients is 0.22 mg or more, per one kilogram of the body weight of the pet, from the viewpoint of obtaining excellent suppressive effect on behavior problems, and that the total dosage is 100 mg or less, per one kilogram of the body weight of the pet, from the viewpoint of costs.

EXAMPLES

The present invention will be described in more detail hereinbelow by means of the working examples, without intending to particularly restrict the present invention thereto.

Example 1

There were reacted 0.3 M glutamine and 1.5 M ethylamine at 30° C. for 22 hours in borate buffer ($Na_2B_4O_7$-NaOH, pH 11) with 0.3 U glutaminase. Glutamic acid, a by-product, was 20 nmol. The purification for the reaction mixture was carried out by applying the reaction mixture to Dowex 50×8 and Dowex 1×2 column chromatography, and eluted with ethanol. From the fact that the isolated substance exhibited the same Rf value as standard substance of theanine when subjected to amino acid analyzer and paper chromatography, the isolated substance from the reaction mixture was theanine. When the isolated substance was hydrolyzed with hydrochloric acid or glutaminase, glutamic acid and ethylamine was formed in a 1:1 proportion by mole. Since the isolated substance was hydrolyzed with glutaminase, it was shown that ethylamine was bound to γ-position of glutamic acid. In addition, it was confirmed with glutamate dehydrogenase that glutamic acid obtained by hydrolysis had an L-form. Finally, the resulting compound was confirmed to be L-theanine. The theanine was used in the subsequent Test Examples.

Example 2

An electrolytic beverage for pets having a composition listed as Example 2 of Table 1 was prepared.

TABLE 1

|  | Ex. 2 | Ex. 3 | Ex. 4 | Comp. Ex. 1 |
|---|---|---|---|---|
| Glucose | 4.32 g | 4.32 g | 4.32 g | 4.32 g |
| Glycine | 1.80 g | 1.80 g | 1.80 g | 1.80 g |
| Sodium Citrate | 1.57 g | 1.57 g | 1.57 g | 1.57 g |
| Sodium Chloride | 1.40 g | 1.40 g | 1.40 g | 1.40 g |
| Potassium Chloride | 0.45 g | 0.45 g | 0.45 g | 0.45 g |
| Theanine Prepared in Example 1 | 4.13 g | 0.55 g | 0.22 g | — |
| Water | 200 ml | 200 ml | 200 ml | 200 ml |

Example 3

An electrolytic beverage for pets having a composition listed as Example 3 of Table 1 was prepared.

Example 4

An electrolytic beverage for pets having a composition listed as Example 4 of Table 1 was prepared.

Comparative Example 1

An electrolytic beverage for pets having a composition listed as Comparative Example 1 of Table 1 was prepared.

Test Example 1

Nine indoor dogs (average age: 1.5 years, average weight: 4.6 kg) exhibiting abnormal barking (aggressive behavior) to the pet owner and destructive behavior of damaging chairs and sofa after the pet owner went out as behavior problems were subjected to a test for suppressing the behavior problems. Each of these 9 indoor dogs was designated "A" to "I," and subjected to the test. Each of the indoor dogs "A" to "H" was administered with a commercially available pet food supplemented with the following components:

"A": 3.8 mg/day of the theanine prepared in Example 1;

"B": 2 mg/day of the theanine prepared in Example 1 and 100 mg/day of DHA-containing fats and oils powder (commercially available from Taiyo Kagaku Co., Ltd., "Sun Coat DY-5," DHA content: 5.0%);

"C": 2 mg/day of the theanine prepared in Example 1 and 300 mg/day of egg yolk oil preparation ("Yolk Oil L-301," commercially available from Taiyo Kagaku Co., Ltd., arachidonic acid content: 1.6%);

"D": 2 mg/day of the theanine prepared in Example 1 and 25 mg/day of egg yolk lecithin preparation ("Yolk Oil MAC-30," commercially available from Taiyo Kagaku Co., Ltd., phosphatidylcholine content: 20%);

"E": 0.2 mg/day of the theanine prepared in Example 1;

"F": 500 mg/day of the theanine prepared in Example 1;

"G": 0.09 mg/day of the theanine prepared in Example 1 and 18 mg/day of DHA-containing fats and oils powder (commercially available from Taiyo Kagaku Co., Ltd., "Sun Coat DY-5," DHA content: 5.0%); and "H": 95 mg/day of the theanine prepared in Example 1 and 7.3 g/day of DHA-containing fats and oils powder (commercially available from Taiyo Kagaku Co., Ltd., "Sun Coat DY-5," DHA content: 5.0%).

"I" was given only the commercially available pet food.

The extent of suppression of the behavior problems was compared with that before administration of the composition of the present invention. The extent of suppression was numerically indicated as shown in Table 2, and recorded. The results are shown in Table 3.

TABLE 2

| No Change | 0 |
|---|---|
| Slight Suppression | 1 |
| Marked Suppression | 2 |
| Cured | 3 |

TABLE 3

|  | Day 1 | Day 3 | Day 5 | Day 7 |
|---|---|---|---|---|
| A | 1 | 2 | 2 | 3 |
| B | 2 | 3 | 3 | 3 |
| C | 2 | 3 | 3 | 3 |
| D | 2 | 3 | 3 | 3 |
| E | 0 | 0 | 1 | 1 |
| F | 1 | 2 | 3 | 3 |
| G | 0 | 1 | 1 | 2 |

TABLE 3-continued

|   | Day 1 | Day 3 | Day 5 | Day 7 |
|---|-------|-------|-------|-------|
| H | 2 | 3 | 3 | 3 |
| I | 0 | 0 | 0 | 0 |

As shown in Table 3, the behavior problems of the indoor dogs each of which was administered with the composition of the present invention were suppressed from Day 1 of administration, except for "E" and "G." Also, a suppressive effect on the behavior problems was recognized in the indoor dogs "T" and "H" which were administered with a large amount of the composition, but only to an extent equivalent to those of "A" to "D."

In addition, when the indoor dog "A" was compared with the indoor dogs "B" and "C," more effective suppressive effect on the behavior problems was recognized in the indoor dogs "B" and "C."

On the other hand, some suppressive effects on the behavior problems were recognized in the indoor dogs "E" and "G" which were administered with a small amount of the composition, but somewhat smaller.

In contrast, however, no suppressive effect on the behavior problems was recognized in the indoor dog "I," which was given only the pet food.

Test Example 2

Nine cats which were castrated or subjected to contraception (5 castrated cats, 4 cats subjected to contraception, average age: 1.2 years, average weight: 3.8 kg) exhibiting behavior problems associated with abnormal urine marking (e.g. spray) were subjected to a test for suppressing the behavior problems. Each of these 9 cats was designated "AA" to "II," and subjected to the test. Each of the cats "AA" to "HH" was administered with a commercially available cat food supplemented with the following components:

"AA": 3.2 mg/day of the theanine prepared in Example 1;
"BB": 1.7 mg/day of the theanine prepared in Example 1 and 83 mg/day of DHA-containing fats and oils powder (commercially available from Taiyo Kagaku Co., Ltd., "Sun Coat DY-5," DHA content: 5.0%);
"CC": 1.7 mg/day of the theanine prepared in Example 1 and 250 mg/day of egg yolk oil preparation ("Yolk Oil L-301," commercially available from Taiyo Kagaku Co., Ltd., arachidonic acid content: 1.6%);
"DD": 1.7 mg/day of the theanine prepared in Example 1 and 21 mg/day of egg yolk lecithin preparation ("Yolk Oil MAC-30," commercially available from Taiyo Kagaku Co., Ltd., phosphatidylcholine content: 20%);
"EE": 0.17 mg/day of the theanine prepared in Example 1;
"FF": 415 mg/day of the theanine prepared in Example 1;
"GG": 0.07 mg/day of the theanine prepared in Example 1 and 15 mg/day of DHA-containing fats and oils powder (commercially available from Taiyo Kagaku Co., Ltd., "Sun Coat DY-5," DHA content: 5.0%); and
"HH": 79 mg/day of the theanine prepared in Example 1 and 6 g/day of DHA-containing fats and oils powder (commercially available from Taiyo Kagaku Co., Ltd., "Sun Coat DY-5," DHA content: 5.0%).
"II" was given only the commercially available cat food.

The extent of suppression of the behavior problems was compared with that before administration of the composition of the present invention. The extent of suppression was numerically indicated as shown in Table 2, and recorded. The results are shown in Table 4.

TABLE 4

|   | Day 1 | Day 3 | Day 5 | Day 7 |
|---|-------|-------|-------|-------|
| AA | 1 | 1 | 2 | 2 |
| BB | 2 | 3 | 3 | 3 |
| CC | 2 | 3 | 3 | 3 |
| DD | 2 | 3 | 3 | 3 |
| EE | 0 | 0 | 1 | 1 |
| FF | 1 | 1 | 2 | 2 |
| GG | 0 | 1 | 1 | 2 |
| HH | 2 | 3 | 3 | 3 |
| II | 0 | 0 | 0 | 0 |

As shown in Table 4, the behavior problems of the cats each of which was administered with the composition of the present invention were suppressed from Day 1 of administration, except for "EE" and "GG." Also, a suppressive effect on the behavior problems was recognized in the cats "FF" and "HH" which were administered with a large amount of the composition, but only to an extent equivalent to those of "AA" to "DD."

In addition, when the cat "AA" was compared with the cats "BB" and "CC," more effective suppressive effect on the behavior problems was recognized in the cats "BB" and "CC."

On the other hand, some suppressive effects on the behavior problems were recognized in the cats "EE" and "GG" which were administered with a small amount of the composition, but somewhat smaller.

In contrast, however, no suppressive effect on the behavior problems was recognized in the cat "II," which was given only the cat food.

Test Example 3

Nine indoor dogs (average age: 1.7 years, average weight: 4.8 kg) with heatstroke were subjected to a test for suppressing the behavior problems associated with heatstroke (e.g., reduced blood pressure, shivering, cryptogenic astasia). Each of these 9 indoor dogs was designated "AAA" to "III," and subjected to the test. Each of the indoor dogs "AAA" to "HHH" was administered with a commercially available pet food supplemented with the following components:

"AAA": 4 mg/day of the theanine prepared in Example 1;
"BBB": 2.2 mg/day of the theanine prepared in Example 1 and 110 mg/day of DHA-containing fats and oils powder (commercially available from Taiyo Kagaku Co., Ltd., "Sun Coat DY-5," DHA content: 5.0%);
"CCC": 2.2 mg/day of the theanine prepared in Example 1 and 320 mg/day of egg yolk oil preparation ("Yolk Oil L-301," commercially available from Taiyo Kagaku Co., Ltd., arachidonic acid content: 1.6%);
"DDD": 2.2 mg/day of the theanine prepared in Example 1 and 27 mg/day of egg yolk lecithin preparation ("Yolk Oil MAC-30," commercially available from Taiyo Kagaku Co., Ltd., phosphatidylcholine content: 20%);
"EEE": 0.3 mg/day of the theanine prepared in Example 1;
"FFF": 530 mg/day of the theanine prepared in Example 1;
"GGG": 0.1 mg/day of the theanine prepared in Example 1 and 20 mg/day of DHA-containing fats and oils powder (commercially available from Taiyo Kagaku Co., Ltd., "Sun Coat DY-5," DHA content: 5.0%); and
"HHH": 100 mg/day of the theanine prepared in Example 1 and 7.7 g/day of DHA-containing fats and oils powder (commercially available from Taiyo Kagaku Co., Ltd., "Sun Coat DY-5," DHA content: 5.0%).
"III" was given only the commercially available pet food.

The extent of suppression of the behavior problems was compared with that before administration of the composition of the present invention. The extent of suppression was numerically indicated as shown in Table 2, and recorded. The results are shown in Table 5.

TABLE 5

|     | Day 1 | Day 3 | Day 5 | Day 7 |
| --- | --- | --- | --- | --- |
| AAA | 1 | 1 | 2 | 2 |
| BBB | 2 | 3 | 3 | 3 |
| CCC | 2 | 3 | 3 | 3 |
| DDD | 2 | 3 | 3 | 3 |
| EEE | 0 | 1 | 1 | 1 |
| FFF | 1 | 1 | 2 | 2 |
| GGG | 0 | 1 | 1 | 2 |
| HHH | 2 | 3 | 3 | 3 |
| III | 0 | 0 | 0 | 0 |

As shown in Table 5, the behavior problems of the indoor dogs each of which was administered with the composition of the present invention were suppressed from Day 1 of administration, except for "EEE" and "GGG." Also, a suppressive effect on the behavior problems was recognized in the indoor dogs "FFF" and "HHH" which were administered with a large amount of the composition, but only to an extent equivalent to those of "AAA" to "DDD."

In addition, when the indoor dog "AAA" was compared with the indoor dogs "BBB" and "CCC," more effective suppressive effect on the behavior problems was recognized in the indoor dogs "BBB" and "CCC."

On the other hand, some suppressive effects on the behavior problems were recognized in the indoor dogs "EEE" and "GGG" which were administered with a small amount of the composition, but somewhat smaller.

In contrast, however, no suppressive effect on the behavior problems recognized in the indoor dog "III," which was given only the pet food.

Test Example 4

Nine indoor dogs (average age: 1.7 years, average weight: 4.8 kg) exhibiting behavior problems associated with kinesia (e.g. reduced blood pressure, astasia, shivering, dysbasia) by riding on the car with the pet owner and being brought to a pet clinic were subjected to a test for suppressing the behavior problems. Each of these 9 indoor dogs exhibited exhausted symptom when arrived to the pet clinic. Each of these 9 indoor dogs was designated "J" to "R," and subjected to the test. Each of the indoor dogs "J" to "Q" was forcibly orally administered with the following components:

"J": 4 mg/day of the theanine prepared in Example 1;
"K": 2.2 mg/day of the theanine prepared in Example 1 and 110 mg/day of DHA-containing fats and oils powder (commercially available from Taiyo Kagaku Co., Ltd., "Sun Coat DY-5," DHA content: 5.0%);
"L": 2.2 mg/day of the theanine prepared in Example 1 and 320 mg/day of egg yolk oil preparation ("Yolk Oil L-301," commercially available from Taiyo Kagaku Co., Ltd., arachidonic acid content: 1.6%);
"M": 2.2 mg/day of the theanine prepared in Example 1 and 27 mg/day of egg yolk lecithin preparation ("Yolk Oil MAC-30," commercially available from Taiyo Kagaku Co., Ltd., phosphatidylcholine content: 20%);
"N": 0.3 mg/day of the theanine prepared in Example 1;
"O": 530 mg/day of the theanine prepared in Example 1;
"P": 0.1 mg/day of the theanine prepared in Example 1 and 20 mg/day of DHA-containing fats and oils powder (commercially available from Taiyo Kagaku Co., Ltd., "Sun Coat DY-5," DHA content: 5.0%); and
"Q": 100 mg/day of the theanine prepared in Example 1 and 7.7 g/day of DHA-containing fats and oils powder (commercially available from Taiyo Kagaku Co., Ltd., "Sun Coat DY-5," DHA content: 5.0%).
"R" was given only the commercially available pet food.

The extent of suppression of the behavior problems was compared with that before administration of the composition of the present invention. The extent of suppression was numerically indicated as shown in Table 2, and recorded. The results are shown in Table 6.

TABLE 6

|   | Hour 1 | Hour 3 | Hour 5 | Hour 7 |
| --- | --- | --- | --- | --- |
| J | 1 | 1 | 2 | 3 |
| K | 3 | 3 | 3 | 3 |
| L | 3 | 3 | 3 | 3 |
| M | 3 | 3 | 3 | 3 |
| N | 0 | 0 | 1 | 1 |
| O | 1 | 1 | 2 | 3 |
| P | 1 | 1 | 1 | 2 |
| Q | 3 | 3 | 3 | 3 |
| R | 0 | 0 | 0 | 0 |

As shown in Table 6, the behavior problems of the indoor dogs each of which was administered with the composition of the present invention were suppressed from Hour 1 of administration, except for "N." Also, a suppressive effect on the behavior problems was recognized in the indoor dogs "O" and "Q" which were administered with a large amount of the composition, but only to an extent equivalent to those of "J" to "M."

In addition, when the indoor dog "J" was compared with the indoor dogs "K" and "L," more effective suppressive effect on the behavior problems was recognized in the indoor dogs "K" and "L."

On the other hand, some suppressive effects on the behavior problems were recognized in the indoor dogs "N" and "P" which were administered with a small amount of the composition, but somewhat smaller.

In contrast, however, no suppressive effect on the behavior problems was recognized in the indoor dog "R," which was given only the pet food.

Test Example 5

Nine aged dogs (average age: 10.4 years, average weight: 5.5 kg) being diagnosed to have dementia and exhibiting behavior problems associated with dementia (e.g. attack, destruction, inappropriate elimination, excess barking, aberrant motor behavior, abnormal vocalizing, dysbasia) were subjected to a test for suppressing the behavior problems. Each of these 9 aged dogs was designated "JJ" to "RR," and subjected to the test. Each of the aged dogs "JJ" to "QQ" was administered with a commercially available pet food supplemented with the following components:

"JJ": 4.6 mg/day of the theanine prepared in Example 1;
"KK": 2.6 mg/day of the theanine prepared in Example 1 and 130 mg/day of DHA-containing fats and oils powder (commercially available from Taiyo Kagaku Co., Ltd., "Sun Coat DY-5," DHA content: 5.0%);
"LL": 2.6 mg/day of the theanine prepared in Example 1 and 370 mg/day of egg yolk oil preparation ("Yolk Oil L-301," commercially available from Taiyo Kagaku Co., Ltd., arachidonic acid content: 1.6%);
"MM": 2.6 mg/day of the theanine prepared in Example 1 and 32 mg/day of egg yolk lecithin preparation ("Yolk Oil MAC-30," commercially available from Taiyo Kagaku Co., Ltd., phosphatidylcholine content: 20%);

"NN": 0.4 mg/day of the theanine prepared in Example 1;
"OO": 610 mg/day of the theanine prepared in Example 1;
"PP": 0.2 mg/day of the theanine prepared in Example 1 and 25 mg/day of DHA-containing fats and oils powder (commercially available from Taiyo Kagaku Co., Ltd., "Sun Coat DY-5," DHA content: 5.0%); and
"QQ": 115 mg/day of the theanine prepared in Example 1 and 8.8 g/day of DHA-containing fats and oils powder (commercially available from Taiyo Kagaku Co., Ltd., "Sun Coat DY-5," DHA content: 5.0%).

"RR" was given only the commercially available pet food.

The extent of suppression of the behavior problems was compared with that before administration of the composition of the present invention. The extent of suppression was numerically indicated as shown in Table 2, and recorded. The results are shown in Table 7.

TABLE 7

| | Day 1 | Week 1 | Week 5 | Week 10 |
|---|---|---|---|---|
| JJ | 1 | 1 | 1 | 1 |
| KK | 1 | 1 | 2 | 2 |
| LL | 1 | 1 | 2 | 2 |
| MM | 1 | 1 | 2 | 3 |
| NN | 0 | 0 | 1 | 1 |
| OO | 1 | 1 | 1 | 1 |
| PP | 0 | 1 | 1 | 2 |
| QQ | 1 | 1 | 2 | 2 |
| RR | 0 | 0 | 0 | 0 |

As shown in Table 7, the behavior problems of the aged dogs each of which was administered with the composition of the present invention were gradually suppressed from Day 1 of administration, except for "NN" and "PP." Also, a suppressive effect on the behavior problems was recognized in the aged dogs "OO" and "QQ" which were administered with a large amount of the composition, but only to an extent equivalent to those of "JJ" to "MM."

In addition, when the aged dog "JJ" was compared with the aged dogs "KK" and "LL," more effective suppressive effect on the behavior problems was recognized in the aged dogs "KK" and "LL."

On the other hand, some suppressive effects on the behavior problems were recognized in the aged dogs "NN" and "PP" which were administered with a small amount of the composition, but somewhat smaller.

In contrast, however, no suppressive effect on the behavior problems was recognized in the aged dog "RR," which was given only the pet food.

Test Example 6

Four indoor dogs (average age: 1.4 years, average weight: 5.1 kg) exhibiting abnormal barking (aggressive behavior) to the pet owner and destructive behavior of damaging chairs and sofa after the pet owner went out as behavior problems were subjected to a test for suppressing the behavior problems. Each of these 4 indoor dogs was designated "a" to "d," and subjected to the test. Each of the indoor dogs "a" to "d" was administered with the following:

"a": 200 ml/day of the electrolytic beverage for pets prepared in Example 2;
"b": 200 ml/day of the electrolytic beverage for pets prepared in Example 3;
"c": 200 mi/day of the electrolytic beverage for pets prepared in Example 4; and
"d": 200 ml/day of the electrolytic beverage for pets prepared in Comparative Example 1.

The extent of suppression of the behavior problems was compared with that before administration of the electrolytic beverage for pets comprising the composition of the present invention. The extent of suppression was numerically indicated as shown in Table 2, and recorded. The results are shown in Table 8.

TABLE 8

| | Day 1 | Day 3 | Day 5 | Day 7 |
|---|---|---|---|---|
| a | 1 | 1 | 2 | 3 |
| b | 1 | 1 | 2 | 3 |
| c | 0 | 1 | 1 | 1 |
| d | 0 | 0 | 0 | 0 |

As shown in Table 8, the behavior problems of the indoor dog "a" which was administered with the electrolytic beverage for pets prepared in Example 2 were suppressed from Day 1 of administration. Also, a suppressive effect on the behavior problems was recognized in the indoor dog "b" which was administered with the electrolytic beverage for pets prepared in Example 3, but only to an extent equivalent to those of "a."

On the other hand, some suppressive effects on the behavior problems were recognized in the indoor dog "c" which was administered with the electrolytic beverage for pets prepared in Example 4, but somewhat smaller.

In contrast, however, no suppressive effect on the behavior problems was recognized in the indoor dog "d," which was administered with the electrolytic beverage for pets prepared in Comparative Example 1.

Test Example 7

Four indoor dogs (average age: 1.8 years, average weight: 5.1 kg) exhibiting behavior problems associated with kinesia by riding on the car with the pet owner and being brought to a pet clinic were subjected to a test for suppressing the behavior problems. Each of these 4 indoor dogs exhibited exhausted symptom when arrived to the pet clinic. Each of these 4 indoor dogs was designated "aa" to "dd," and subjected to the test. Each of the indoor dogs "aa" to "dd" was administered with the following:

"aa": 200 mi/day of the electrolytic beverage for pets prepared in Example 2;
"bb": 200 ml/day of the electrolytic beverage for pets prepared in Example 3;
"cc": 200 ml/day of the electrolytic beverage for pets prepared in Example 4; and
"dd": 200 ml/day of the electrolytic beverage for pets prepared in Comparative Example 1.

The extent of suppression of the behavior problems was compared with that before administration of the electrolytic beverage for pets comprising the composition of the present invention. The extent of suppression was numerically indicated as shown in Table 2, and recorded. The results are shown in Table 9.

TABLE 9

| | Hour 3 | Hour 6 | Hour 12 | Hour 24 |
|---|---|---|---|---|
| aa | 1 | 1 | 2 | 3 |
| bb | 1 | 1 | 2 | 3 |
| cc | 0 | 0 | 1 | 2 |
| dd | 0 | 0 | 0 | 0 |

As shown in Table 9, the behavior problems of the indoor dog "aa" which was administered with the electrolytic beverage for pets prepared in Example 2 were suppressed from Hour 1 of administration. Also, a suppressive effect on the behavior problems was recognized in the indoor dog "bb"which was administered with the electrolytic beverage for pets prepared in Example 3, but only to an extent equivalent to those of "aa."

On the other hand, some suppressive effects on the behavior problems were recognized in the indoor dog "cc" which was administered with the electrolytic beverage for pets prepared in Example 4, but somewhat smaller.

In contrast, however, no suppressive effect on the behavior problems was recognized in the indoor dog "dd," which was administered with the electrolytic beverage for pets prepared in Comparative Example 1.

Since the composition for suppressing behavior problems of pets, which is an inventive product, can be administered in the form supplemented to usually used pet foods and electrolytic beverages, the composition can be used very highly conveniently, and is also free from problems concerning protecting an animal from harm, thereby giving significant effects. In addition, no harmful action to pets such as side effects is recognized, in contrary to conventionally used pharmaceuticals.

Thus, the present invention greatly contributes not only to pet industries but also to solving problems concerning protecting an animal from harm.

EQUIVALENT

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A composition for suppressing behavior problems of pets, comprising theanine, and one or more compounds selected from the group consisting of cholines, arachidonic acid, eicoapentaenoic acid (EPA) and docosahexaenoic acid (DHA).

2. A method of suppressing behavior problems in pets, comprising administering to a pet having behavior problems a composition comprising theanine, and one or more compounds selected from the group consisting of cholines, arachidonic acid, eicoapentaenoic acid (EPA) and docosahexaenoic acid (DHA).

3. The method according to claim 2, wherein the composition is used such that the dosage of theanine per administration is 0.05 to 100 mg, per one kilogram of the body weight of the pet.

4. The method according to claim 2, wherein the composition is used such that the dosage of theanine per administration is 0.02 to 20 mg, per one kilogram of the body weight of the pet, and the total dosage of said one or more compounds selected from the group consisting of cholines, arachidonic acid, eicoapentaenoic acid (EPA) and docosahexaenoic acid (DHA) per administration is 0.2 to 80 mg, per one kilogram of the body weight of the pet.

5. The method according to claim 2, wherein the pet is at least one animal selected from the group consisting of dogs, cats, rabbits, hamsters, guinea pigs, rats, mice, parakeets, parrots and Lonchura striates.

6. The method according to claim 2, wherein at least one behavior problem is suppressed, said behavior problem selected from the group consisting of attack, destruction, inappropriate elimination, licking its paw repeatedly, scratching, crytogenic astasia, shivering, astasia, spray, reduced blood pressure, abnormal appestat associated with adynamia, aberrant motor behavior, dysbasia, abnormal sense, abnormal posture, abnormal vocalizing, loss of feeling, loss of interrelation and abnormal situation judgement.

\* \* \* \* \*